United States Patent
Idowu et al.

(10) Patent No.: US 9,398,871 B2
(45) Date of Patent: Jul. 26, 2016

(54) DEVICES, SYSTEMS AND METHODS FOR INSERTING A GASTROINTESTINAL BODY PART INTO A PATIENTS BODY WHILE MEASURING OXYGEN SATURATION

(71) Applicant: Children's Hospital & Research Center Oakland, Oakland, CA (US)

(72) Inventors: Olajire Idowu, Lafayette, CA (US); Sunghoon Kim, San Ramon, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 0 days.

(21) Appl. No.: 14/327,870

(22) Filed: Jul. 10, 2014

(65) Prior Publication Data

US 2015/0018652 A1  Jan. 15, 2015

Related U.S. Application Data

(60) Provisional application No. 61/845,846, filed on Jul. 12, 2013.

(51) Int. Cl.
*A61F 2/50* (2006.01)
*A61B 5/1455* (2006.01)
*A61B 17/34* (2006.01)
(Continued)

(52) U.S. Cl.
CPC ............ *A61B 5/14551* (2013.01); *A61B 5/6846* (2013.01); *A61B 17/3423* (2013.01); *A61B 5/4255* (2013.01); *A61B 2017/00818* (2013.01); (Continued)

(58) Field of Classification Search
CPC ........... A61B 2503/045; A61B 5/6846; A61B 5/14557; A61B 5/4255; A61B 2017/00818; A61B 2018/00494
See application file for complete search history.

(56) References Cited

U.S. PATENT DOCUMENTS 4,637,061 A   1/1987  Riese
6,467,956 B1  10/2002 Tilman et al.
(Continued)

FOREIGN PATENT DOCUMENTS

RU   2157662   10/2000

OTHER PUBLICATIONS

Kim, Sunghoon, et al., "Use of pulse oximeter placed on a gastroschisis silo to monitor intestinal oxygen saturation," (2006), Pediatr Surg Int, 22: 763-765.*

(Continued)

*Primary Examiner* — Catherine B Kuhlman
*Assistant Examiner* — Shannon McBride
(74) *Attorney, Agent, or Firm* — Michael B. Rubin; Bozicevic, Field & Francis LLP

(57) ABSTRACT

Devices for containing exposed internal body parts during their insertion into the body of a patient are provided. The devices include a surgical pouch that comprises a measurement feature adapted to facilitate a measurement of the oxygen saturation of the exposed internal body parts. In some embodiments, the subject devices comprise an inner pouch for containing the exposed internal body parts, as well as an outer pouch that can be pressurized to exert positive pressure on the inner pouch to facilitate insertion of the internal body parts into the body of the patient. Also provided are methods for containing the exposed internal body parts of a patient and inserting the body parts into the patient, optionally using positive pressure, while monitoring the oxygen saturation of the exposed internal body parts via the measurement feature.

11 Claims, 11 Drawing Sheets

(51) Int. Cl.
*A61B 5/00* (2006.01)
*A61B 17/00* (2006.01)
*A61B 18/00* (2006.01)

(52) U.S. Cl.
CPC ............... *A61B 2017/00876* (2013.01); *A61B 2018/00494* (2013.01); *A61B 2503/045* (2013.01)

(56) References Cited

U.S. PATENT DOCUMENTS

| | | | |
|---|---|---|---|
| 2012/0209060 A1 | 8/2012 | Kim et al. | |
| 2013/0019374 A1* | 1/2013 | Schwartz | A61F 5/00 2/69 |
| 2013/0211378 A1* | 8/2013 | Miller | A61M 5/16859 604/508 |

OTHER PUBLICATIONS

Fischer, James D., et al., (1995), "Gastroschisis: A Simple Technique for Staged Silo Closure," Journal of Pediatric Surgery, 30(8): 1169-1171.*

Corbitt et al., (2008) "Parents' Resource Guide: Gastroschisis" Nationwide Children's Hospital Brochure, 6 pages.

Fischer, James D., et al., (1995), "Gastroschisis: A Simple Technique for Staged Silo Closure", Journal of Pediatric Surgery, 30(8):1169-1171.

Kidd, J.N., et al., (2001), "Staged reduction of gastroschisis: a simple method", Pediatric Surgery International, 17:242-244.

Dabbas, Natalie, et al., (2009), "GABBY: An ex vivo model for learning and refining the technique of preformed silo application in the management of gastroschisis", African Journal of Paediatric Surgery, 6(2):73-76.

* cited by examiner

DEVICES, SYSTEMS AND METHODS FOR INSERTING A GASTROINTESTINAL BODY PART INTO A PATIENTS BODY WHILE MEASURING OXYGEN SATURATION

CROSS-REFERENCE TO RELATED APPLICATIONS

Under 35 U.S.C. §119(e), this application claims priority to the filing date of U.S. Provisional Patent Application Ser. No. 61/845,846, filed on Jul. 12, 2013, the disclosure of which application is herein incorporated by reference in its entirety.

INTRODUCTION

Physicians may be presented at times with a patient whose internal body parts are protruding outside the body due to, e.g., birth defects or trauma. These exposed internal body parts must be put back inside the patient during treatment. One example situation where this condition occurs is with gastroschisis. Gastroschisis (also called paraomphalocele, laparoschisis, abdominoschisis, or abdominal hernia) is a type of inherited congenital abdominal wall defect in which the intestines (and sometimes other organs) develop outside the fetal abdomen through an opening in the abdominal wall near the site of the umbilicus. In gastroschisis, the abdominal wall does not close properly, and the stomach, small bowel, and/or large intestine may have come through the small opening near the umbilical cord. Within the womb, these internal body parts are floating freely in the amniotic fluid and may not typically present any harm to the fetus; however, once born, the baby will require immediate attention to correct the developmental defect.

Surgical pouches, such as sterile plastic or silicone bags, often referred to as "silo" bags, are typically placed around the exposed internal body parts and used to contain the exposed internal body parts so that they may be shielded from trauma, infection, and dehydration until the body parts can be put back within the body. Often the exposed internal body parts may be swollen and inflamed and require time before the swelling and inflammation subside to permit the internal body parts to be safely put back within the body. Insertion of the exposed internal body parts is typically a gradual process, often taking up to about a week to complete.

Insertion may include assistance from gravity and/or assistance from the physician. For example, the physician may gently push part of the internal body parts back into the body opening, or a surgical pouch may be suspended above the abdomen during the insertion process so that the exposed internal body parts can gradually re-enter the abdomen. In some instances, as the swelling subsides and the abdomen becomes more accustomed to the presence of a greater number of internal body parts, portions of the exposed internal body parts may be inserted into the patient's body.

SUMMARY

Devices for containing exposed internal body parts during their insertion into the body of a patient are provided. The devices include a surgical pouch that comprises a measurement feature adapted to facilitate a measurement of the oxygen saturation of the exposed internal body parts. In some embodiments, the subject devices comprise an inner pouch for containing the exposed internal body parts, as well as an outer pouch that can be pressurized to exert positive pressure on the inner pouch to facilitate insertion of the internal body parts into the body of the patient. Also provided are methods for containing the exposed internal body parts of a patient and inserting the body parts into the patient, optionally using positive pressure, while monitoring the oxygen saturation of the exposed internal body parts via the measurement feature.

In some embodiments, the present disclosure provides a device for containing an exposed gastrointestinal body part during insertion of the body part into the body of a patient, the device including a surgical pouch for containing an exposed gastrointestinal body part of the patient, wherein the surgical pouch includes a measurement feature adapted to facilitate a measurement of the oxygen saturation of the exposed gastrointestinal body part, and a securing component adapted to secure an opening of the device to a surgical opening on the patient.

In some embodiments, the surgical pouch includes an inner pouch for containing the exposed gastrointestinal body part of the patient, and an outer pouch for exerting positive pressure on the inner pouch to facilitate the insertion of the exposed gastrointestinal body part into the patient's body, wherein the outer pouch includes a port that provides access to an area between the inner pouch and the outer pouch.

In some embodiments, the securing component includes a ring positioned around the perimeter of the opening of the device. In some embodiments, the ring is collapsible for insertion into the surgical opening on the patient, and the ring is resilient, such that the ring returns to an un-collapsed state after insertion into the surgical opening on the patient. In some embodiments, the ring includes a spring. In some embodiments, the ring includes a magnetic component. In some embodiments, the securing component includes a first ring and a second ring, and each of the first ring and the second ring includes a magnetic component.

In some embodiments, the device comprises a coupling component disposed at a distal end of the device and adapted to couple the distal end of the device to a support structure. In some embodiments, the coupling component includes a reinforcing material. In some embodiments, the measurement feature includes a material that is different from the material of the surgical pouch. In some embodiments, the measurement feature is positioned adjacent the securing component. In some embodiments, the measurement feature includes a finger-like projection that is adapted to receive an exposed gastrointestinal body part therein. In some embodiments, the measurement feature includes a molded window that is adapted to receive an exposed gastrointestinal body part therein.

In some embodiments, the present disclosure provides a method for containing and monitoring an exposed gastrointestinal body part of a patient, the method involving placing the exposed gastrointestinal body part inside of a device to contain the exposed gastrointestinal body part, wherein the device includes a surgical pouch for containing a gastrointestinal body part of the patient, wherein the surgical pouch includes a measurement feature adapted to facilitate a measurement of the oxygen saturation of the exposed gastrointestinal body part, and a securing component adapted to secure an opening of the device to a surgical opening on the patient, placing a portion of the exposed gastrointestinal body part into the measurement feature of the device, and monitoring the oxygen saturation of the exposed gastrointestinal body part via the measurement feature.

In some embodiments, the device includes an inner pouch for containing the exposed gastrointestinal body part of the patient, and an outer pouch for exerting positive pressure on the inner pouch to facilitate the insertion of the exposed gastrointestinal body part into the patient's body, wherein the outer pouch includes a port that provides access to an area between the inner pouch and the outer pouch, and wherein the method involves pressurizing the outer pouch of the device to facilitate insertion of the exposed gastrointestinal body part into the patient's body.

In some embodiments, monitoring the oxygenation of the exposed gastrointestinal body part via the measurement feature involves attaching a pulse oximeter to the measurement feature. In some embodiments, the securing component of the device includes a ring positioned around the perimeter of the opening of the device. In some embodiments, the ring is collapsible for insertion into the surgical opening on the patient, and the ring is resilient, such that the ring returns to an un-collapsed state after insertion into the surgical opening on the patient. In some embodiments, the ring includes a spring.

In some embodiments, the device further includes a coupling component disposed at a distal end of the device and adapted to couple the distal end of the device to a support structure, and the method further involves coupling the coupling component to a support structure. In some embodiments, the coupling component of the device further includes a reinforcing material. In some embodiments, the methods involve placing a lubricant in the area between the inner pouch and the outer pouch of the device. In some embodiments, monitoring the oxygen saturation of the exposed gastrointestinal body part via the measurement feature involves attaching a pulse oximeter to the external surface of the measurement feature. In some embodiments, the measurement feature includes a material that is different from the material of the surgical pouch. In some embodiments, the measurement feature includes a finger-like projection that is adapted to receive an exposed gastrointestinal body part therein. In some embodiments, the measurement feature includes a molded window that is adapted to receive an exposed gastrointestinal body part therein.

In some embodiments, the present disclosure provides a system for containing and monitoring an exposed gastrointestinal body part of a patient, the system including a device including a surgical pouch for containing a gastrointestinal body part of the patient, wherein the surgical pouch includes a measurement feature adapted to facilitate a measurement of the oxygen saturation of the exposed gastrointestinal body part, and a securing component adapted to secure an opening of the device to a surgical opening on the patient, a support structure adapted to support the device, and a monitoring device for monitoring the oxygen saturation of the exposed gastrointestinal body part of the patient.

In some embodiments, the surgical pouch of the device includes an inner pouch for containing the exposed gastrointestinal body part of the patient, and an outer pouch for exerting positive pressure on the inner pouch to facilitate the insertion of the exposed gastrointestinal body part into the patient's body, wherein the outer pouch comprises a port that provides access to an area between the inner pouch and the outer pouch. In some embodiments, the securing component includes a first ring and a second ring, wherein each of the first ring and the second ring includes a magnetic component, and wherein the second ring is adapted to provide for a magnetic force with the magnetic component of the first ring when in use.

In some embodiments, the present disclosure provides a kit including a plurality of devices having different dimensions, wherein each device includes a surgical pouch for containing a gastrointestinal body part of a patient, wherein the surgical pouch includes a measurement feature adapted to facilitate a measurement of the oxygen saturation of the exposed gastrointestinal body part, and a securing component adapted to secure an opening of the device to a surgical opening on the patient.

DETAILED DESCRIPTION

Figure 1:
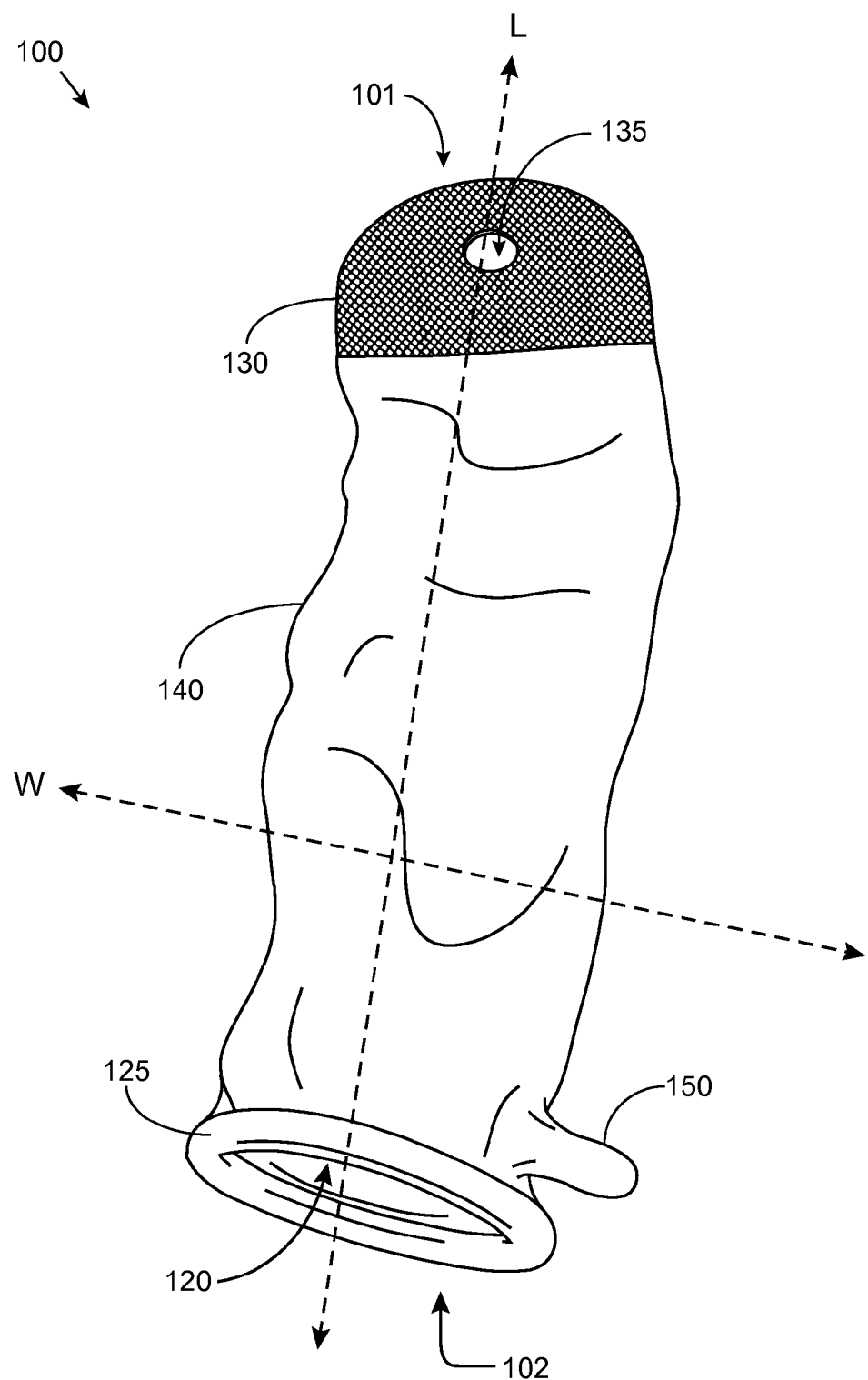
FIG. 1 illustrates a perspective view of a device in accordance with some embodiments of the invention for inserting exposed internal body parts into a patient's body.

Devices for containing exposed internal body parts during their insertion into the body of a patient are provided. The devices include a surgical pouch that comprises a measurement feature adapted to facilitate a measurement of the oxygen saturation of the exposed internal body parts. In some embodiments, the subject devices comprise an inner pouch for containing the exposed internal body parts, as well as an outer pouch that can be pressurized to exert positive pressure on the inner pouch to facilitate insertion of the internal body parts into the body of the patient. Also provided are methods for containing the exposed internal body parts of a patient and inserting the body parts into the patient, optionally using positive pressure, while monitoring the oxygen saturation of the exposed internal body parts via the measurement feature.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the invention in greater detail, aspects of the systems and devices of various embodiments are reviewed first in greater detail, followed by a discussion of methods and kits according to certain embodiments of the invention.

Systems and Devices

Aspects of the disclosure include systems and devices configured for use in containing a plurality of exposed internal body parts of a patient, such as, e.g., exposed gastrointestinal body parts, such as the stomach, small bowel, and/or large intestine, and inserting the exposed gastrointestinal body parts into the patient's body. The subject devices generally include a distal end and a proximal end. The term "proximal end," as used herein, refers to the end of the device, component or member thereof that is nearest to the patient during use. The term "distal end," as used herein, refers to the end of the device, component or member thereof that is furthest from the patient during use. For example, the distal end of a pouch is the end of the pouch that is closest to the distal end of the device. Likewise, the proximal end of a pouch is the end of the pouch that is the closest to the proximal end of the device. The term "longitudinal axis," as used herein, refers to the axis that extends between the proximal end and the distal end of the device. The term "latitudinal axis," as used herein, refers to the axis that is perpendicular to the longitudinal axis. It should be appreciated that the distal end of a component of the device is the end of the component that is closest to the distal end of the device.

The subject devices generally include a surgical pouch that includes a measurement feature adapted to facilitate a measurement of the oxygen saturation of the exposed gastrointestinal body parts that are placed inside the device. In some embodiments, the surgical pouch comprises an inner pouch and an outer pouch. The subject devices also generally include a securing component that, in use, secures the device to the patient's body. Each of these and other components is now further described in greater detail.

Surgical Pouch

Aspects of the invention include a surgical pouch that is generally used to contain an exposed gastrointestinal body part, e.g., the stomach, small bowel, and/or large intestine of a patient. The surgical pouch generally has an opening at the proximal end of the device that leads into an internal portion of the surgical pouch. The surgical pouch generally comprises a body that extends along the longitudinal axis of the device to a position near the distal end of the device, and has a dimension along the longitudinal axis of the device that is generally greater than its latitudinal dimension. The surgical pouch is open at its proximal end, and is generally closed, or sealed at its distal end.

The surgical pouch may comprise various shapes. For example, in some instances, the shape of the surgical pouch may be cylindrical or substantially cylindrical. For example, the opening at the proximal end of the surgical pouch may be circular, and the body of the surgical pouch may cylindrically extend from the circular opening to the distal end, where the pouch is closed, or sealed. In some embodiments, the closed distal end of the surgical pouch may have a circular shape, while in some embodiments the closed distal end of the surgical pouch may have a dome shape. In other instances, a seam may be provided at the distal end of the surgical pouch that closes off the pouch along a line in the direction of the latitudinal axis.

The dimensions of the surgical pouch may vary depending on the particular application and/or the size of the patient. In some embodiments, the latitudinal dimension of the surgical pouch is generally the same as the latitudinal dimension of the opening of the device. In some embodiments, the latitudinal dimension of the surgical pouch may vary as the distance from the opening varies along the longitudinal axis of the device. For example, in some embodiments, the latitudinal dimension of the surgical pouch may decrease as the distance from the opening increases along the longitudinal axis. In some embodiments, the latitudinal dimension of the surgical pouch may increase as the distance from the opening increases along the longitudinal axis, while in some embodiments the latitudinal dimension of the surgical pouch may remain constant as the distance from the opening increases along the longitudinal axis. In some embodiments, the latitudinal dimension of the surgical pouch may range from about 1 inch, up to about 2 inches, up to about 3 inches, up to about 4 inches, up to about 5 inches, up to about 6 inches or more. In some embodiments, the longitudinal dimension of the surgical pouch may range from about 4 inches, up to about 6 inches, up to about 8 inches, up to about 10 inches, up to about 12 inches, up to about 14 inches, up to about 16 inches, up to about 18 inches, up to about 20 inches, up to about 22 inches, up to about 24 inches, up to about 26 inches, up to about 28 inches, or up to about 30 inches or more.

The surgical pouch may generally be made of any suitable flexible medical-grade material that can contact an exposed internal body part without eliciting a negative response. Suitable materials generally include, but are not limited to, sterile or sterilizable plastics, such as polyethylene, polypropylene, and silicone. In use, the surgical pouch may generally be collapsed, or deformed as the exposed internal organs that are placed therein are gradually inserted into the patient's body. As such, the surgical pouch can generally be collapsed (e.g., by the application of positive pressure) from an extended resting state, and the volume of the surgical pouch can be progressively reduced as the surgical pouch is collapsed towards the opening of the device.

In some embodiments, the subject devices may include a surgical pouch that comprises an inner pouch disposed within an outer pouch. In such embodiments, the inner pouch is adapted to hold an exposed gastrointestinal body part of the patient. The inner pouch is disposed within the outer pouch to define a space between the exterior wall of the inner pouch and the inner wall of the outer pouch, which space can be filled with pressurized air. Introduction of pressurized air into the space defined by the inner and outer pouch walls exerts pressure on the inner pouch so as to facilitate insertion of the exposed gastrointestinal body part into the body of the patient.

In embodiments that include an inner pouch and an outer pouch, the inner pouch and the outer pouch generally originate at an origination point that is located at a position along the body of the surgical pouch that is longitudinally separated from the proximal end of the device by a distance. The inner pouch and the outer pouch may be connected to one another at the origination point by sealing, joining, or otherwise attaching the material of the outer pouch to the material of the inner pouch. In some embodiments, the connection between the material of the inner pouch and the material of the outer pouch at the origination point is air-tight, such that pressure is maintained at a desired level following introduction of pressurized air or gas inside the outer pouch. In some embodiments, the origination point of the inner pouch and the outer pouch is located at a position that is about 0.5 inches, up to about 0.75 inches, up to about 1 inch, up to about 1.25 inches, up to about 1.5 inches, up to about 1.75 inches, up to about 2 inches, up to about 2.25 inches, up to about 2.5 inches, up to about 2.75 inches, up to about 3 inches, up to about 3.25 inches, or up to about 3.5 inches distal to the opening of the device along the longitudinal axis.

The outer pouch and the inner pouch generally comprise a body that extends from the origination point along the longitudinal axis of the device towards the distal end of the device, and has a dimension along the longitudinal axis of the device that is generally longer than its latitudinal dimension. At its proximal end, the outer pouch is connected to an external surface of the surgical pouch, and is generally closed, or sealed, at its distal end. The outer pouch generally extends further along the longitudinal axis than the inner pouch, and generally surrounds the inner pouch, forming a space between the outer pouch and the inner pouch. The distal end of the inner pouch is generally closed, or sealed.

The inner pouch and the outer pouch may include various shapes. For example, in some instances, the shape of the inner pouch and the outer pouch may be cylindrical or substantially cylindrical. For example, the proximal end of the inner pouch and the outer pouch may be circular in shape, and the body of the inner pouch and the outer pouch cylindrically extends from the proximal end to the distal end, where each pouch is closed, or sealed. For example, in some embodiments, the closed distal end of each pouch may have a circular shape, while in some embodiments the closed distal end of each pouch may have a dome shape. In other instances, a seam may be provided at the distal end of each pouch that closes off the pouch along a line in the direction of the latitudinal axis.

The dimensions of the inner pouch and the outer pouch may vary depending on the particular application and/or the size of the patient. In some embodiments, the latitudinal dimension of each pouch is generally the same as the latitudinal dimension of the opening of the device. In some embodiments, the latitudinal dimension of the outer pouch and/or the inner pouch may vary as the distance from the origination point varies along the longitudinal axis of the device. For example, in some embodiments, the latitudinal dimension of the outer pouch and/or the inner pouch may increase as the distance from the origination point increases along the longitudinal axis. In some embodiments, the latitudinal dimension of the outer pouch and/or the inner pouch may remain constant as the distance from the origination point increases along the longitudinal axis. In some embodiments, the latitudinal dimension of the outer pouch and/or the inner pouch may range from about 1 inch, up to about 2 inches, up to about 3 inches, up to about 4 inches, up to about 5 inches, up to about 6 inches or more. In some embodiments, the longitudinal dimension of the outer pouch and/or the inner pouch may range from about 4 inches, up to about 6 inches, up to about 8 inches, up to about 10 inches, up to about 12 inches, up to about 14 inches, up to about 16 inches, up to about 18 inches, up to about 20 inches, up to about 22 inches, up to about 24 inches, up to about 26 inches, up to about 28 inches, up to about 30 inches or more, up to about 32 inches, up to about 34 inches, or up to about 36 inches or more.

Each pouch may generally be made of any suitable flexible medical-grade material. Suitable materials generally include, but are not limited to sterile or sterilizable plastics, such as polyethylene, polypropylene, and silicone. In use, the outer pouch may generally be pressurized to exert pressure on the inner pouch. As such, the outer pouch is generally configured to withstand a given amount of positive pressure without bursting or breaking. In some embodiments, the outer pouch is configured to receive a pressurized liquid or gas having a pressure ranging from about 1 atm, up to about 2 atm, up to about 3 atm, up to about 4 atm, or up to about 5 atm or more.

In some embodiments, the outer pouch may comprise a port, or opening, that allows access to a space between the inner pouch and the outer pouch. The port may generally be air-tight and sealable, such that a pressurized liquid or gas can be introduced into the space between the inner and outer pouches via the port, and the port may then be closed to retain the pressurized liquid or gas within the space, thereby exerting a positive pressure on the inner pouch. The port may generally be located at any convenient position on the external surface of the outer pouch. In some embodiments, the port is located at or near the distal end of the outer pouch. In some embodiments, the port is located at or near the proximal end of the outer pouch. In some embodiments, the port is located at a position between the proximal end and the distal end of the outer pouch, such as, e.g., at a suitable position along the body of the outer pouch.

In some embodiments, the surgical pouch may include a coupling component disposed on the distal end that allows the device to be removably coupled to a support structure so that the device may hang above the patient. In embodiments wherein the surgical pouch comprises an outer pouch and an inner pouch, the outer pouch may comprise a coupling component at its distal end. In some embodiments, the distal end of the device may be hung above the opening of the device via the coupling component, such that gravity facilitates the movement of the patient's internal organs in a downward direction, through the opening of the device, and into the patient's body.

In some instances, the coupling component may comprise a layer of material having a hole within it that enables it to hang from a rod, hook, bar, etc., of an external support structure, for example. The layer of material may also serve to reinforce the distal end of the inner pouch so that it may hang without ripping, tearing, or otherwise becoming damaged, and also serve to provide a seam that closes off the distal end of the inner pouch. The coupling component may comprise any of a variety of elements for various coupling mechanisms, such as clamps, hooks, hinges, adhesives, strings for tying, hooks, loops, snap-fit elements (e.g., buttons, etc.), etc. In some embodiments, the coupling component may comprise one or more reinforcing materials that provide enhanced mechanical stability to the coupling component, e.g., to prevent tearing or ripping of the device material when the device is hung from an external support structure. For example, in some embodiments the coupling component may comprise a layer of mesh that is embedded in the material of the outer pouch to provide enhanced mechanical support to the device. Suitable reinforcing materials include, but are not limited to, biomedical textiles, such as, e.g., woven and non-woven mesh materials, polymeric materials, such as, e.g., nylon, and the like.

Measurement Feature

In some embodiments, the subject devices may comprise a measurement feature that is adapted to receive a portion of the patient's exposed gastrointestinal body part therein. The measurement feature is generally adapted so that a sufficient amount of the patient's gastrointestinal body part, e.g., the patient's stomach, small bowel, and/or large intestine, can be placed within the measurement feature to facilitate taking a measurement of the exposed internal body part with an externally-applied monitoring device. Such can be, for example, a relatively small portion of tissue of a gastrointestinal body part (e.g., a small portion of bowel tissue). The measurement feature is generally adapted so that an externally-applied monitoring device, such as, e.g., a pulse oximeter, can be easily attached to the external surface of the measurement feature to facilitate taking measurements, such as oxygen saturation measurements, for the purpose of verifying that the exposed gastrointestinal body part that has been placed within the device is receiving a sufficient supply of oxygenated blood.

In some embodiments, the measurement feature may comprise a material whose properties facilitate taking an oxygen saturation measurement of the exposed gastrointestinal body part that has been placed therein. For example, in some embodiments, a measurement feature comprises a material that is different from the material of the surgical pouch. In certain embodiments, the material of the measurement feature is transparent or substantially transparent to light, such that light emitted by, e.g., a pulse oximeter, may pass through the material of the measurement feature and through the exposed gastrointestinal body part to provide a measurement of the oxygen saturation of the exposed gastrointestinal body part. In some embodiments, the material of the measurement feature is more transparent to light than the material of the surgical pouch. Examples of transparent or substantially transparent materials include, but are not limited to, polyethylene, polypropylene, polystyrene and silicone. In certain embodiments, the thickness of the material that makes up the measurement feature may be less than the thickness of the material that makes up, e.g., the body of the surgical pouch. The reduced thickness of the material in the region of the measurement feature facilitates the passage of light through the measurement feature, which in turn facilitates accurate measurement of, e.g., the oxygen saturation of the exposed gastrointestinal body part using a pulse oximeter. In some embodiments, the measurement feature is made from the same material as the surgical pouch, and in some embodiments, the material of the measurement feature has the same thickness as the material of the surgical pouch.

Measurement features in accordance with embodiments of the invention can have any suitable shape and dimensions. In some embodiments, the latitudinal dimension of a measurement feature ranges from about 0.25 inches, up to about 0.5 inches, up to about 0.75 inches, up to about 1 inch, up to about 1.25 inches, up to about 1.5 inches, up to about 1.75 inches, or up to about 2 inches or more. In some embodiments, the longitudinal dimension of a measurement feature ranges from about 0.25 inches, up to about 0.5 inches, up to about 0.75 inches, up to about 1 inch, up to about 1.25 inches, up to about 1.5 inches, up to about 1.75 inches, or up to about 2 inches or more.

In some embodiments, a measurement feature may be formed by extending, from the body of the surgical pouch, a finger-like projection into which the exposed internal body parts may be placed. In some embodiments, the base of the finger-like projection is contiguous with the outer surface of the body of the surgical pouch, such that the finger-like projection extends from the body of the surgical pouch in a latitudinal direction. In such embodiments, the projection length of the finger-like projection can range from about 0.25 inches, up to about 0.5 inches, up to about 0.75 inches, up to about 1 inch, up to about 1.25 inches, up to about 1.5 inches, up to about 1.75 inches, or up to about 2 inches or more. The finger-like projection is generally made from a flexible material so that the projection itself is flexible and can be manipulated to place, e.g., a portion of bowel tissue inside the projection and attach a measurement component, such as, e.g., a pulse oximeter, on the projection.

In some embodiments, a measurement feature may comprise a rigid or semi-rigid molded window that is placed along the body of the surgical pouch such that one or more inwardly-directed components of the molded window protrude into the interior of the surgical pouch. The inwardly-directed components of the molded window can form a measurement feature that is accessible from the external surface of the device. In some embodiments, the components of the molded window have a suitable geometry and suitable dimensions to facilitate the attachment of an external monitoring device, such as, e.g., a pulse oximeter. For example, in some embodiments, the geometry and dimensions of the components of the molded window are such that an external monitoring device can be easily attached thereto. The molded window is generally made from rigid or semi-rigid materials so that the window will hold its shape and facilitate the placement of a measurement component on the external surface of the molded window.

The measurement feature is generally located at a suitable position along the body of the surgical pouch to facilitate taking a measurement of the portion of the exposed gastrointestinal body part that is placed inside the device. In some embodiments, the measurement feature is located adjacent the securing component, which is described further below. In embodiments that include an inner pouch and an outer pouch, the measurement feature is generally located at a position along the body of the surgical pouch between the proximal end of the device and the origination point of the inner and outer pouches.

Securing Component

Aspects of the invention include a securing component that is adapted to secure an opening of the device to a surgical opening on a patient's body. By "surgical opening" is meant an opening in the skin of the patient's body, either naturally-occurring (as due to a birth defect), created by trauma, or created by a surgeon, through which an internal cavity of the patient, such as the abdominal cavity, may be accessed.

In some embodiments, the securing component is capable of collapsing (i.e., is collapsible, or deformable) for insertion into a surgical opening on the patient's body, and is capable of returning to an un-collapsed state once inserted into the surgical opening. In some embodiments, the securing component may comprise a ring made from a resilient material that can be deformed in order to insert the securing component into the surgical opening on the patient's body. After insertion into the surgical opening, the ring returns to its non-deformed state to secure the device to the patient's body. In some embodiments, the securing component may comprise a spring or another resilient material or structure. In some embodiments, the securing component may comprise an adhesive material that makes contact with the patient's body and adheres to the patient's body.

The securing component generally functions to secure the device to the patient's body, and is disposed around the periphery of the opening of the device to maintain alignment between the opening of the device positioned within the patient's abdomen and a surgical opening on the patient's body. The securing component is generally sized to be larger than the surgical opening in its non-collapsed state, such that once the securing component has been placed inside the patient and returned to its non-collapsed state, it is larger than the surgical opening, and cannot pass through the surgical opening without being deformed or collapsed.

In some embodiments, the securing component may comprise one or more chambers that can be inflated with a gas or filled with a medium, such as, e.g., water, to secure the device to the patient. For example, in some embodiments the securing component may comprise one or more chambers that are inflated with air once the securing component has been placed inside the patient. Inflating the chambers helps to secure the device in place and maintain alignment between the opening of the device and the surgical opening on the patient's body.

In certain embodiments, the securing component may comprise a ring, as described above, wherein the ring optionally comprises one or more magnetic component(s) disposed within a lumen defined by the ring. In such embodiments, the securing component can optionally be used in combination with a second ring comprising one more magnetic components, which second ring is adapted to be removably disposed around the outside of the surgical pouch. In use, the first ring is positioned within the abdomen of the patient, and the second ring is positioned around the surgical pouch and outside the abdominal wall of the patient. In use, the magnetic forces between the magnetic component(s) of the first ring and the second ring can facilitate the positioning of the first ring within the abdomen of the patient and can thus facilitate securing the surgical pouch in place in the patient. Optionally, the manipulation of the second ring can facilitate manipulation of the abdominal wall disposed between the first and second rings.

By "magnetic component" is meant a magnet or a material that is attracted to a magnet, such as, e.g., a ferromagnetic material. Magnetic components are selected for use in the first and second rings as described herein so as to provide for a magnetic attraction between the magnetic component(s) of the first ring and the magnetic component(s) of the second ring. Magnetic components may be rigid or flexible. In general, the magnetic component(s) of the first ring are selected and/or positioned so as to allow for sufficient flexibility of the first ring to accommodate placement of the first ring within the abdomen of the patient during use.

In some embodiments, the magnetic component may be composed of a single magnetic ring or a plurality of individual magnetic components, which plurality may include two, three, four, five, six, or more magnetic components. For example, in some embodiments a magnetic component may include a plurality of beads, rods, discs, and the like, which may be, e.g., deformable or bendable and capable of being, e.g., stacked or aligned to form a ring shape and disposed inside the lumen of the first and/or second rings of the securing component.

In some embodiments, the individual magnetic components of the first and/or second rings may be evenly spaced along the ring, while in other embodiments the individual magnetic components may be grouped together in clusters, which clusters may be evenly or unevenly spaced throughout the ring. For example, in some embodiments, several small clusters of magnetic components (e.g., stackable magnetic discs) may be placed at specific locations within or around the first and/or second ring so as to provide e.g., two, three, four, five, six or more small clusters of magnetic components. In some such embodiments, the clusters may be evenly spaced or substantially evenly spaced, such that the amount of space in between each of the clusters is the same or is approximately the same. The number of magnetic components in the first ring and in the second ring may be the same or different (e.g., two, three, four, five, six, or more magnetic components in the first and/or second rings). In some embodiments, the number of magnetic components in the first ring are greater than in second ring.

In certain embodiments, the one or more magnetic components may be embedded in a medium disposed within the lumen defined by the ring, such as a gel, e.g., a silicone gel. Such medium can facilitate stabilizing the position of the magnetic components within the ring lumen, e.g., to maintain a desired separation between the individual magnetic components or clusters of magnetic components within the ring and/or to facilitate alignment with magnetic components of a second ring (e.g., as described below).

The first and second rings of the securing component have a diameter ranging from about 1 inch, up to about 2 inches, up to about 3 inches, up to about 4 inches, up to about 5 inches, up to about 6 inches or more. The circumference of the first and second rings is proportional to each ring's diameter. As such, the circumference of the first and second rings ranges from about 3 inches, up to about 6 inches, up to about 9 inches, up to about 12 inches, up to about 15 inches, up to about 18 inches or more. In some embodiments, the one or more magnetic components disposed inside the lumen of the ring(s) may be spaced along the circumference of the ring(s) such that the magnetic components, or clusters of magnetic components, are separated from one another by a distance ranging from about 0.5 inches, up to about 1 inch, up to about 1.5 inches, up to about 2 inches, up to about 2.5 inches, up to about 3 inches, up to about 3.5 inches, up to about 4 inches, up to about 4.5 inches, up to about 5 inches, up to about 5.5 inches, up to about 6 inches, up to about 6.5 inches, up to about 7 inches, up to about 7.5 inches, up to about 8 inches, up to about 8.5 inches, up to about 9 inches or more.

In some embodiments, the magnetic components of the first ring and, optionally, the second ring may be deformable so as to allow the first and/or second ring to be flexible to facilitate manipulation of the first and/or second rings. For example, such deformable magnetic components of the first ring allow the first ring to be of sufficient flexibility so that it may be deformed to allow placement of the securing component inside the patient's body. In some embodiments, the magnetic components of the first and/or second ring may be rigid, but may be spaced inside the ring(s) such that the ring(s) can be deformed, e.g., to allow placement of the first ring inside the patient's body and/or to allow positioning of the second ring around the surgical pouch and on the outside of the patient's abdomen. For example, in some embodiments, a plurality of magnetic components may be spaced around the first and/or second ring so that the ring(s) may be deformed at one or more locations that are not occupied by a magnetic component to facilitate use, e.g., insertion of the first ring into the abdomen, and/or positioning of the second ring to facilitate securing of the device with respect to the patient's body.

In some embodiments, a securing component may comprise a first ring that is attached to a portion of the surgical pouch, such as, e.g., disposed around the opening of the surgical pouch, and may also comprise a second ring that is adapted to be removably disposed around the outside of the surgical pouch. In such embodiments, both the first ring and the second ring may comprise one or more magnetic components, as described above, such that the one or more magnetic components in the first ring are attracted to the one or more magnetic components in the second ring. In use, the first ring may be deformed and placed inside the patient's body during placement of the securing component, while the second ring is positioned around the outside of the surgical pouch and is placed against the patient's skin on the outside of the patient's body near the proximal end of the pouch such that the first and second rings are positioned on opposite sides of the patient's abdominal wall. As noted above, the one or more magnetic components of the first ring are attracted to the one or more magnetic components of the second ring through the patient's abdominal wall, and together the first and second rings help to secure the surgical pouch in place.

In some embodiments, the second ring is attached to a garment that can be worn by the patient. For example, the second ring can be sewn into a garment so as to be disposed around an opening suitable for receiving the surgical pouch. In another example, the second ring can be attached to a tether, which tether is attached to a garment worn by the patient.

In use, the second ring may be periodically lifted or pulled in a direction away from the patient's body to stretch the abdominal wall and the abdominal cavity by exerting a magnetic attraction force on the first ring, and thereby pulling on the first ring when the second ring is lifted or pulled. Such pulling and stretching may aid in the reduction of the one or more gastrointestinal body parts that have been placed within the surgical pouch.

In some embodiments, the first ring and the second ring may each comprise a plurality of spaced-apart magnetic components, and the first and second rings may be rotated with respect to one another, as desired by a caregiver, e.g., so that the magnetic components of the second ring align with the magnetic components of the first ring. When the magnetic components in both rings are aligned, the magnetic attraction between the rings facilitates securing the device in place within the abdomen. For example, after insertion of the first ring, the second ring can be positioned around the surgical pouch and opposite the first ring, and then rotated with respect to the first ring so as to align the magnetic components of the first and second rings so that the magnetic attraction forces between the magnetic components of the first and second rings are sufficient to hold the rings in position. When it is desired to manipulate the device (e.g., to remove the surgical pouch), the second ring can be rotated with respect to the first ring so as to disrupt alignment of the magnetic components and decrease the magnetic attraction between the first and second rings.

When the first and second rings are in place such that the magnetic components are sufficiently aligned, the magnetic force between the first and second rings can be used to manipulate the abdominal wall disposed between the rings. For example, a caregiver can pull the second ring in a direction away from the patient's body so as to stretch the abdominal wall disposed between the first and second rings.

At any time during treatment as may be desired, the rings may be rotated with respect to one another such that the magnetic components are no longer aligned, and as such, the magnetic attraction between the rings is substantially decreased. Thus this embodiment of the device provides the caregiver with flexibility in adjusting therapy as may be needed, e.g., to avoid damaging the patient's tissue, to manipulate the surgical pouch, and the like.

As described above, the subject devices generally include an opening through which an exposed gastrointestinal body part of the patient may be received. The opening may vary in shape, e.g., may be circular, elliptical, square, polygonal, or any other regular or irregular shape. The size of the opening may vary depending on the particular application and/or the size of the patient. For example, in some embodiments, the latitudinal dimension of the opening of the device may range from about 1 inch, up to about 2 inches, up to about 3 inches, up to about 4 inches, up to about 5 inches, or up to about 6 inches or more.

The securing component may also vary in shape, e.g., may be circular, elliptical, square, polygonal, or any other regular or irregular shape. In some embodiments, the opening is circular and the securing element is a ring positioned around the perimeter of the opening. The ring may be collapsible, for instance, and may be inserted into the surgical opening while it is collapsed. The ring may also be resilient, for instance, and may return to an un-collapsed state after being inserted into the patient's body so that it is secured behind the inner wall of the patient's body near the surgical opening. This minimizes the likelihood that the device will detach from the patient. For example, in some embodiments, the ring may comprise a polymeric material that is resilient in nature. In some instances, the ring may further include a spring or spring-like structure made from metal, metal alloys, polymers, etc.

To remove the device, an operator (e.g., a physician, physician's assistant, etc.) may collapse the securing element so that it may be passed through the surgical opening. It should also be appreciated that the securing component may be removed from the surgical opening by gently pulling on the device with enough force to cause the securing component to collapse under pressure from the internal wall of the patient's body at the surgical opening. The ease by which the securing component may be collapsed under such pressure will depend on how flexible, or how easily collapsible, the securing component is. The securing component may generally be made of any suitable flexible medical-grade material that can contact the patient's body without eliciting a negative response. Suitable materials generally include, but are not limited to, sterile or sterilizable plastics, such as polyethylene, polypropylene, and silicone.

Systems and Components

The present disclosure generally provides systems and components thereof that may be used in conjunction with the above-described devices to monitor the oxygen saturation of an exposed gastrointestinal body part of a patient while containing and inserting the body part into the patient's body. Aspects of the subject systems may include a support structure that can be used to support the subject devices in a desirable position. For example, in some embodiments, a support structure may comprise a bar, a hook, a rod, or any other suitable component to which the coupling component of the surgical pouch can be coupled. In some embodiments, a support structure may be extendable, such that the height and/or the position of the support structure can be adjusted to optimally suspend the device above the patient, or in a desirable position.

Aspects of the subject systems may include a monitoring device, such as, e.g., a pulse oximeter, that may be used to take a measurement of the oxygen saturation of the patient's exposed gastrointestinal body part. In some embodiments, a subject monitoring device may have a measurement component that attaches to the measurement feature on the surgical pouch of a subject device to facilitate taking a measurement of the oxygen saturation of the patient's exposed gastrointestinal body part.

Turning now to FIGS. 1-12, various example embodiments of the subject devices are depicted.

FIG. 1 illustrates a perspective view of a device in accordance with some embodiments of the invention for inserting an exposed gastrointestinal body part into a patient's body. As shown, device 100 includes a surgical pouch 140. A distal end 101 and a proximal end 102 of the device are shown for reference purposes. Also shown for reference purposes are a longitudinal axis L and a latitudinal axis W.

The depicted surgical pouch 140 includes an opening 120 with a securing component 125 surrounding the opening. The securing component 125 is depicted as a ring that is collapsible and resilient in nature. The securing component 125 may be collapsed to fit within a surgical opening in the body (e.g., abdomen) of a patient. In such case, the securing component 125 bends and deforms (e.g., to form a narrow elliptical shape) to enable the securing component 125 to pass through the surgical opening. The securing component 125 may then return to its circular shape once inside the body to secure the device to the inner wall of the body. Securing component 125 may be made from, e.g., a polymeric material that is resilient so as to allow the securing component 125 to collapse or deform and then return to its un-collapsed or non-deformed state.

Device 100 also includes a coupling component 130 that can be used to couple the distal end 101 of the device 100 to an external support structure (not shown) so that the distal end 101 may hang above the proximal end 102 of the device 100. The coupling component 130 is shown comprising a layer of material that includes a hole 135 that may be used to hang the distal end 101 of the device 100 from an external support structure.

The surgical pouch 140 of the depicted device 100 comprises a measurement feature 150 in the form of a finger-like projection that extends from the body of the surgical pouch 140. The measurement feature 150 may be used to take measurements from an exposed gastrointestinal body part that is placed inside the measurement feature.

Figure 2:
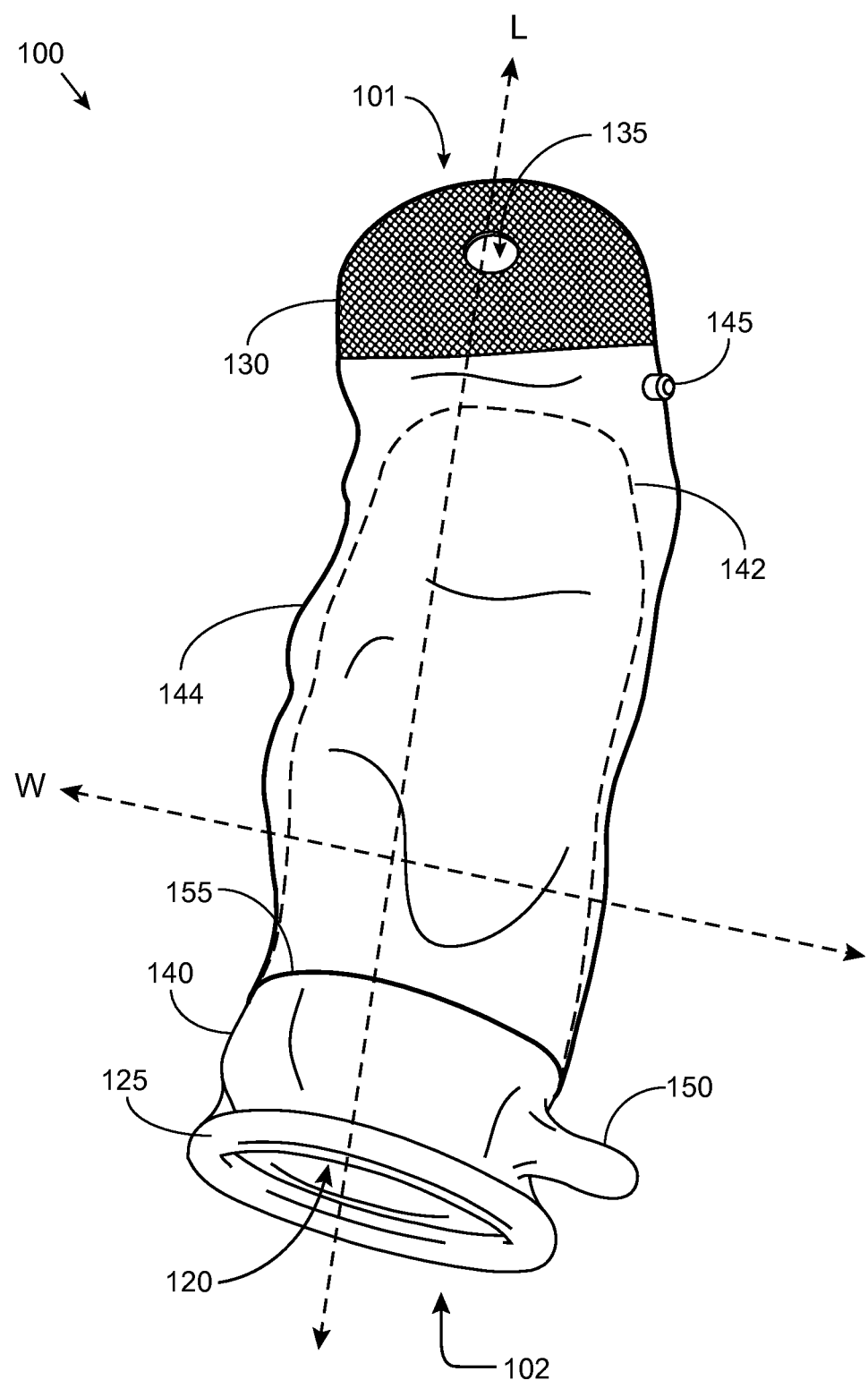
FIG. 2 illustrates a perspective view of a device in accordance with some embodiments of the invention for inserting exposed internal body parts into a patient's body using positive pressure.

FIG. 2 illustrates a perspective view of a device in accordance with some embodiments of the invention for inserting an exposed gastrointestinal body part into a patient's body using positive pressure. As shown, device 100 comprises a surgical pouch 140 that includes an inner pouch 142 and an outer pouch 144. A distal end 101 and a proximal end 102 of the device are shown for reference purposes. Also shown for reference purposes are a longitudinal axis L and a latitudinal axis W.

The depicted surgical pouch 140 includes an opening 120 with a securing component 125 surrounding the opening. The securing component 125 is depicted as a ring that is collapsible and resilient in nature. The securing component 125 may be collapsed to fit within a surgical opening in the body (e.g., abdomen) of a patient. In such case, the securing component 125 bends and deforms (e.g., to form a narrow elliptical shape) to enable the securing component 125 to pass through the surgical opening. The securing component 125 may then return to its circular shape once inside the body to secure the device to the inner wall of the body. Securing component 125 may be made from, for example, a polymeric material that is resilient so as to allow the securing component 125 to collapse or deform and then return to its un-collapsed or non-deformed state.

Device 100 also includes a coupling component 130 that can be used to couple the distal end 101 of the device 100 to an external support structure (not shown) so that the distal end 101 may hang above the proximal end 102 of the device 100. The coupling component 130 is shown comprising a layer of material that includes a hole 135 that may be used to hang the distal end 101 of the device 100 from an external support structure. The outer pouch 144 includes a port 145 that can be used to access a space between the inner pouch 142 and the outer pouch 144. The port 145 is sealable so that a pressurized liquid or gas may be passed through the port, and then the port may be sealed to contain the pressurized liquid or gas in the space between the inner pouch 142 and the outer pouch 144. The inner pouch 142 and the outer pouch 144 originate at an origination point 155 that is located at a position along the body of the surgical pouch 140.

The surgical pouch 140 of the depicted device 100 comprises a measurement feature 150 in the form of a finger-like projection that extends from the body of the surgical pouch 140. The measurement feature 150 may be used to take measurements from an exposed gastrointestinal body part that is placed inside the measurement feature.

Figure 3:
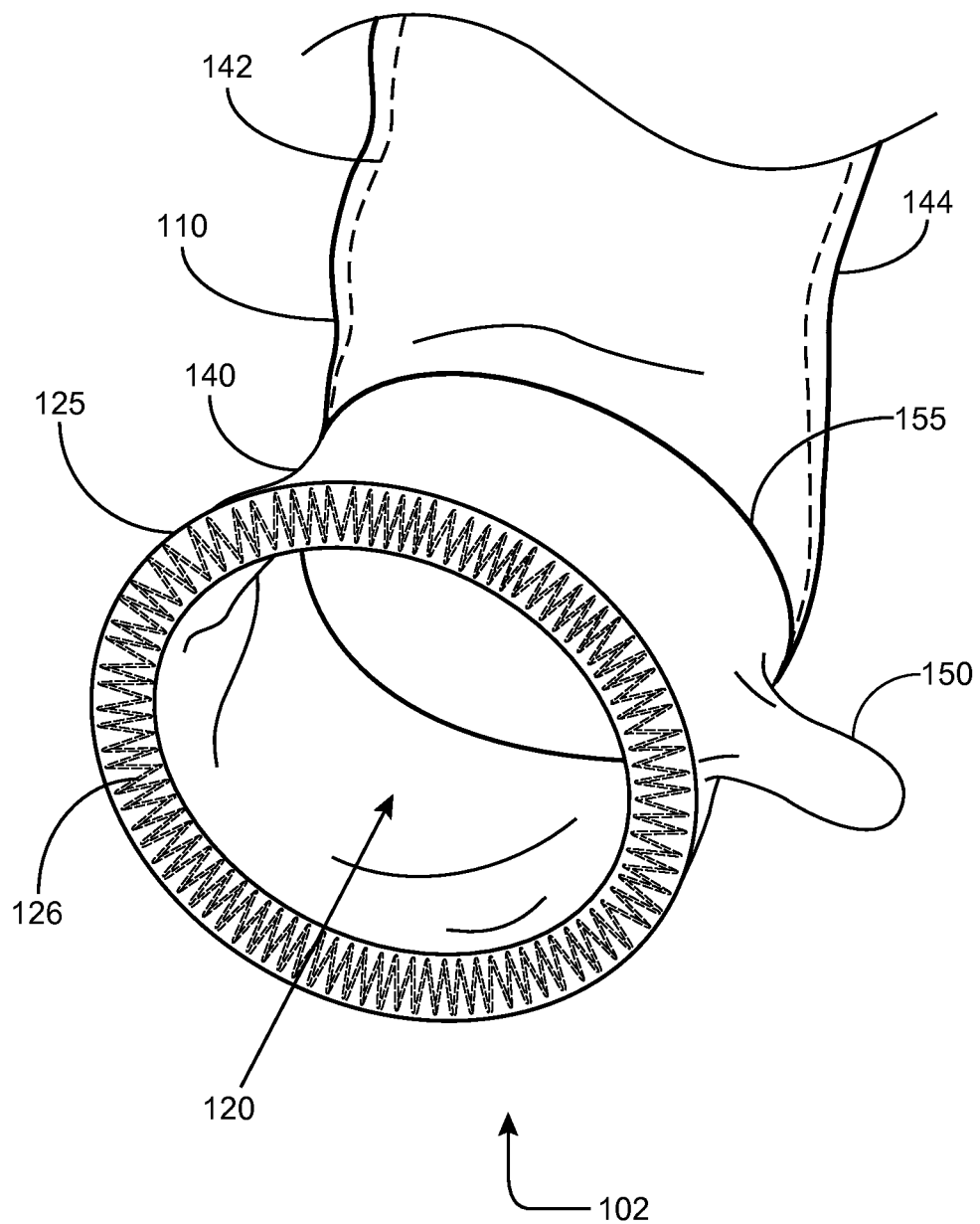
FIG. 3 illustrates a close-up perspective view of a securing component in accordance with some embodiments of the invention.

FIG. 3 illustrates a close-up perspective view of a securing component in accordance with some embodiments of the invention. The proximal end 102 is shown for reference. As shown, securing component 125 comprises a ring disposed around the opening 120 of the surgical pouch 140. In the embodiment shown, securing component 125 includes a spring 126 made from, e.g., a metal or metal alloy. The spring 126 provides the securing component 125 with the collapsible and resilient properties that facilitate entry into a surgical opening and securing to the inner wall of the body of the patient. The securing component 125 is shown enclosed within the polymeric material of the surgical pouch 140 surrounding the opening 120. In other embodiments, the securing element 125 may be coupled to the pouch by other means that attach, connect, or otherwise couple the securing element 125 to the surgical pouch 140 near the opening 120.

As shown, inner pouch 142 and the outer pouch 144 originate at an origination point 155 that is located at a position along the body of the surgical pouch 140. Additionally, a measurement feature 150 is depicted in the form of a finger-like projection that extends from the body of the surgical pouch 140.

Figure 4:
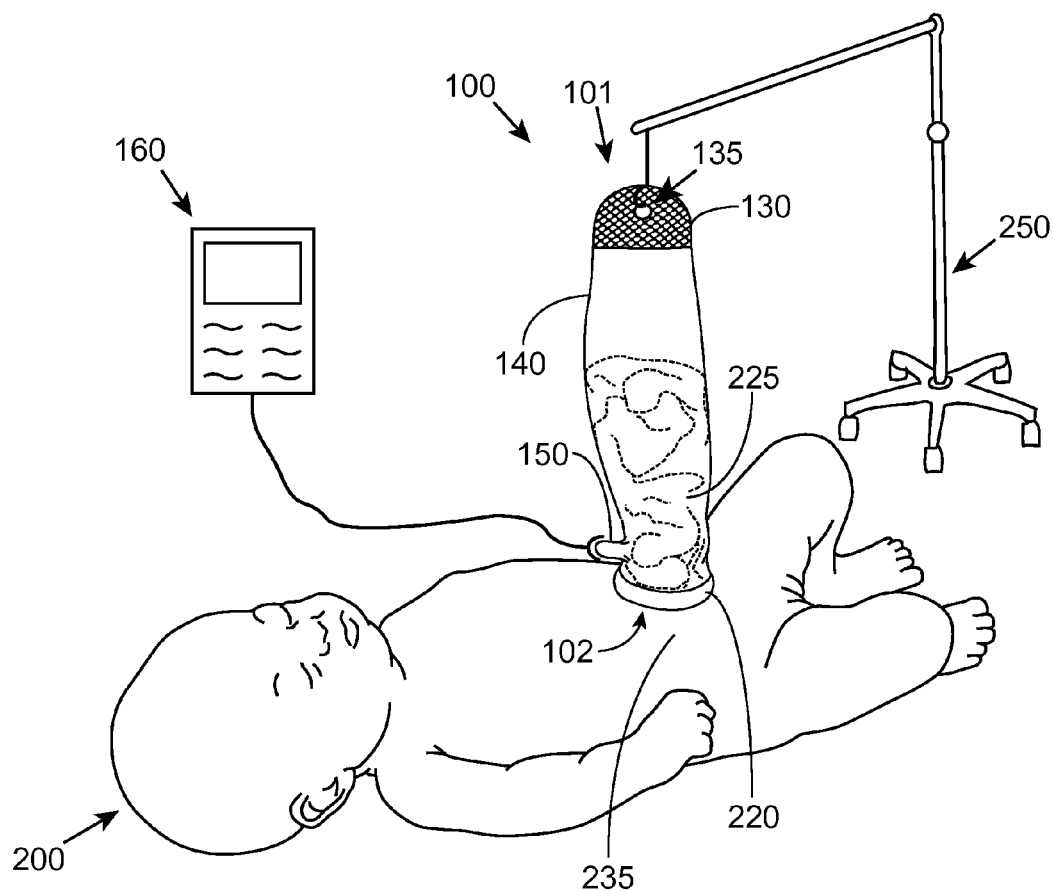
FIG. 4 illustrates a perspective view of the device shown in FIG. 1 containing exposed internal body parts. Also depicted is a monitoring device used to monitor the oxygen saturation of the exposed internal body parts during the insertion process via a measurement feature.

FIG. 4 illustrates a perspective view of the device shown in FIG. 1 during use, according to some embodiments of the invention. Distal end 101 and proximal end 102 are shown for reference purposes. As shown, device 100 includes a surgical pouch 140. Surgical pouch 140 includes a coupling component 130 with a hole 135 that can be coupled to an external support structure 250 to support the device in a desirable position.

An exposed gastrointestinal body part 225 of a patient 200 has been inserted into the surgical pouch 140 and contained therein. An opening (not shown) of the device is located at the proximal end 102 and inserted within a surgical opening 220 in the abdomen 235 of the patient 200. The surgical pouch 140 also includes a measurement feature in the form of a finger-like projection into which the exposed gastrointestinal body part 225 of the patient 200 may be placed. As depicted in FIG. 4, a monitoring device 160, such as, e.g., a pulse oximeter, may be used to monitor the exposed gastrointestinal body part 225 during the insertion process via the measurement feature.

Figure 5:
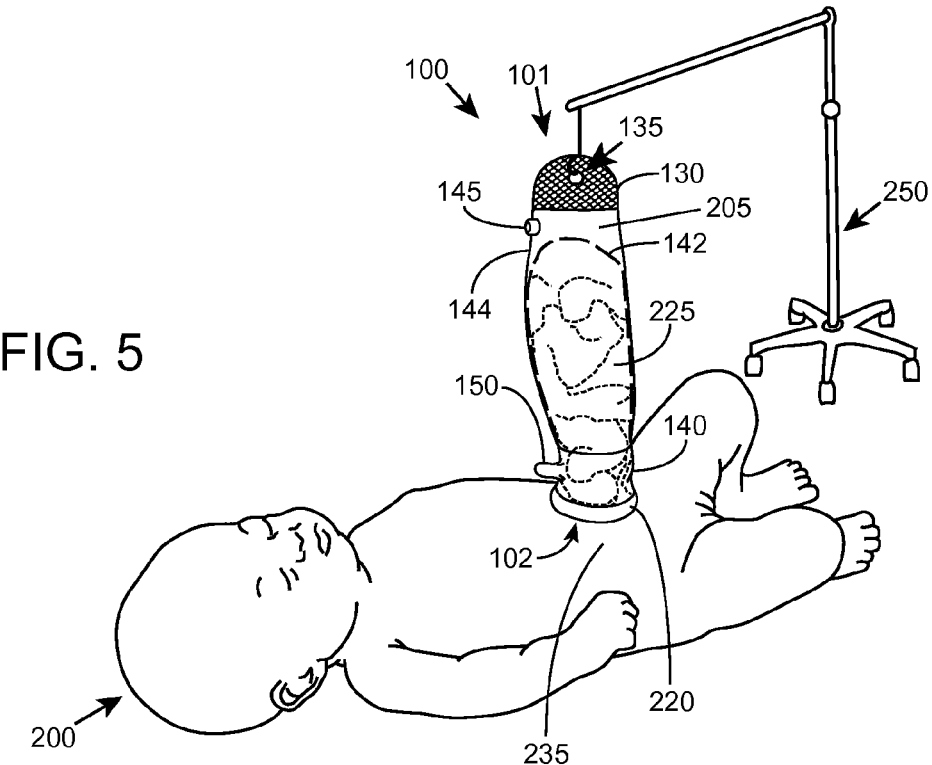
FIG. 5 illustrates a perspective view of the device shown in FIG. 2 containing exposed internal body parts before pressurized air has been introduced into the device.
Figure 6:
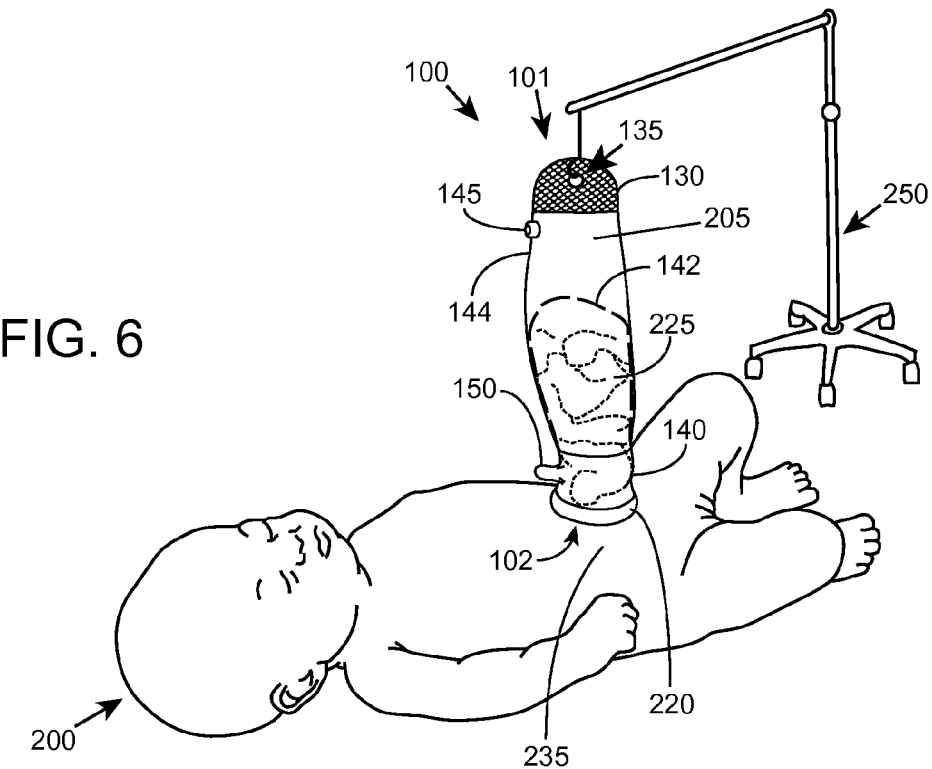
FIG. 6 illustrates a perspective view of the device shown in FIG. 2 containing exposed internal body parts after pressurized air has been introduced into the device and the exposed internal body parts have been partially inserted into the patient's body.
Figure 7:
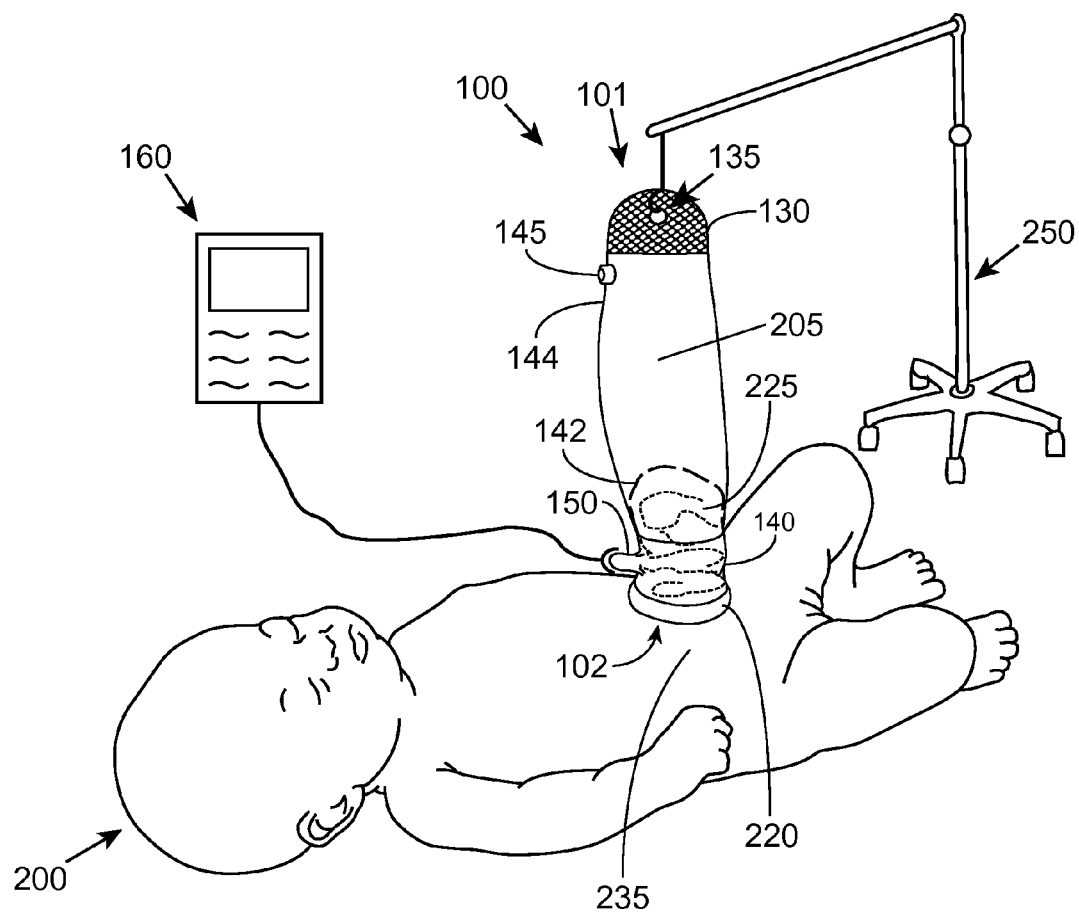
FIG. 7 illustrates a perspective view of the device shown in FIG. 2 containing exposed internal body parts after pressurized air has been introduced into the device and the exposed internal body parts have been partially inserted into the patient's body. Also depicted is a monitoring device used to monitor the oxygen saturation of the exposed internal body parts during the insertion process via a measurement feature.

FIGS. 5-7 illustrate a perspective view of the device shown in FIG. 2 at different times during use, according to some embodiments of the invention. Distal end 101 and proximal end 102 are shown for reference purposes. As shown in the figures, device 100 includes a surgical pouch 140 that comprises an outer pouch 144 and an inner pouch 142. Outer pouch 144 includes a port 145 that can be used to introduce a pressurized liquid or gas into the space 205 formed between the inner pouch 142 and the outer pouch 144. The surgical pouch 140 includes a coupling component 130 with a hole 135 that can be coupled to an external support structure 250 to support the device in a desirable position.

An exposed gastrointestinal body part 225 of a patient 200 has been inserted into the surgical pouch 140 and contained therein. An opening (not shown) of the device is located at the proximal end 102 and inserted within a surgical opening 220 of the abdomen 235 of the patient 200. The surgical pouch 140 also includes a measurement feature in the form of a finger-like projection into which the exposed gastrointestinal body part 225 of the patient 200 may be placed. As depicted in FIG. 7, a monitoring device, such as a pulse oximeter, may be used to monitor the exposed gastrointestinal body part 225 during the insertion process via the measurement feature.

Figure 8:
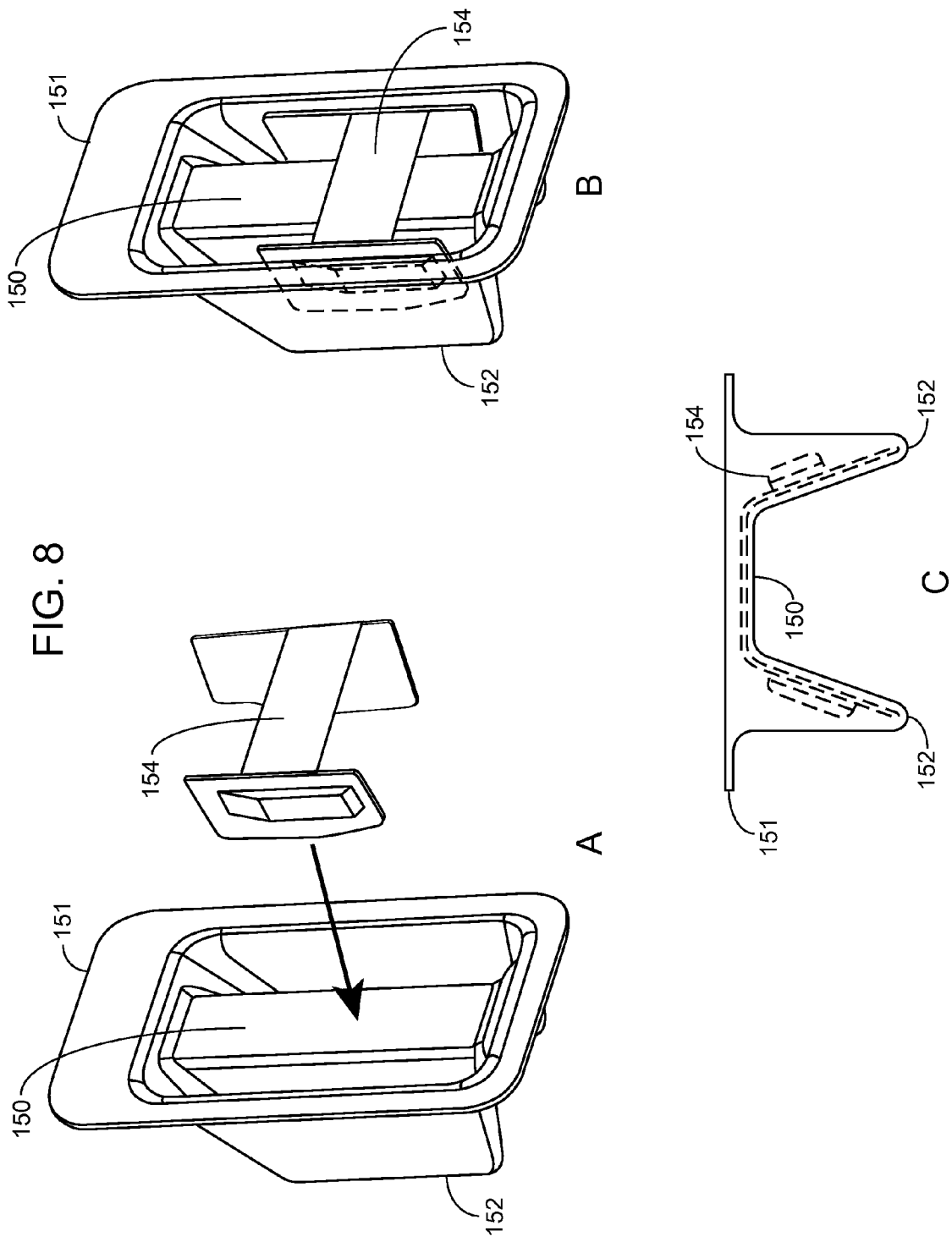
FIG. 8, Panels A-C illustrate different views of a measurement feature in the form of a molded window that is present in some embodiments of the invention to facilitate monitoring of the exposed internal body parts during the insertion process.

FIG. 8, panels A-C illustrate three different views of a measurement feature that may be present in some embodiments of the invention to facilitate monitoring of the exposed gastrointestinal body part. The depicted measurement feature includes a molded window made from, e.g., silicone, that can be placed along the body of the surgical pouch to form a plurality of indentations therein. The molded window includes an outer portion 151 that is mounted flush with the outer surface of the body of the surgical pouch, as well as a plurality of inwardly-directed components 152 that protrude into the interior of the surgical pouch to create a measurement feature that is accessible from the external surface of the device. As depicted in FIG. 8, panel A, a measurement component 154 of a monitoring device (not shown) may easily be placed within a portion of the molded window 150 to facilitate measurements of an exposed gastrointestinal body part of the patient. FIG. 8, panel B shows a perspective view of a molded window measurement feature 150 wherein a measuring component 154 of a monitoring device is engaged with the inwardly-directed components 152 of the molded window 150. FIG. 8, panel C shows an end view of a molded window measurement feature 150 wherein a measuring component 154 of a monitoring device is engaged with the inwardly-directed components 152 of the molded window 150.

Figure 9:
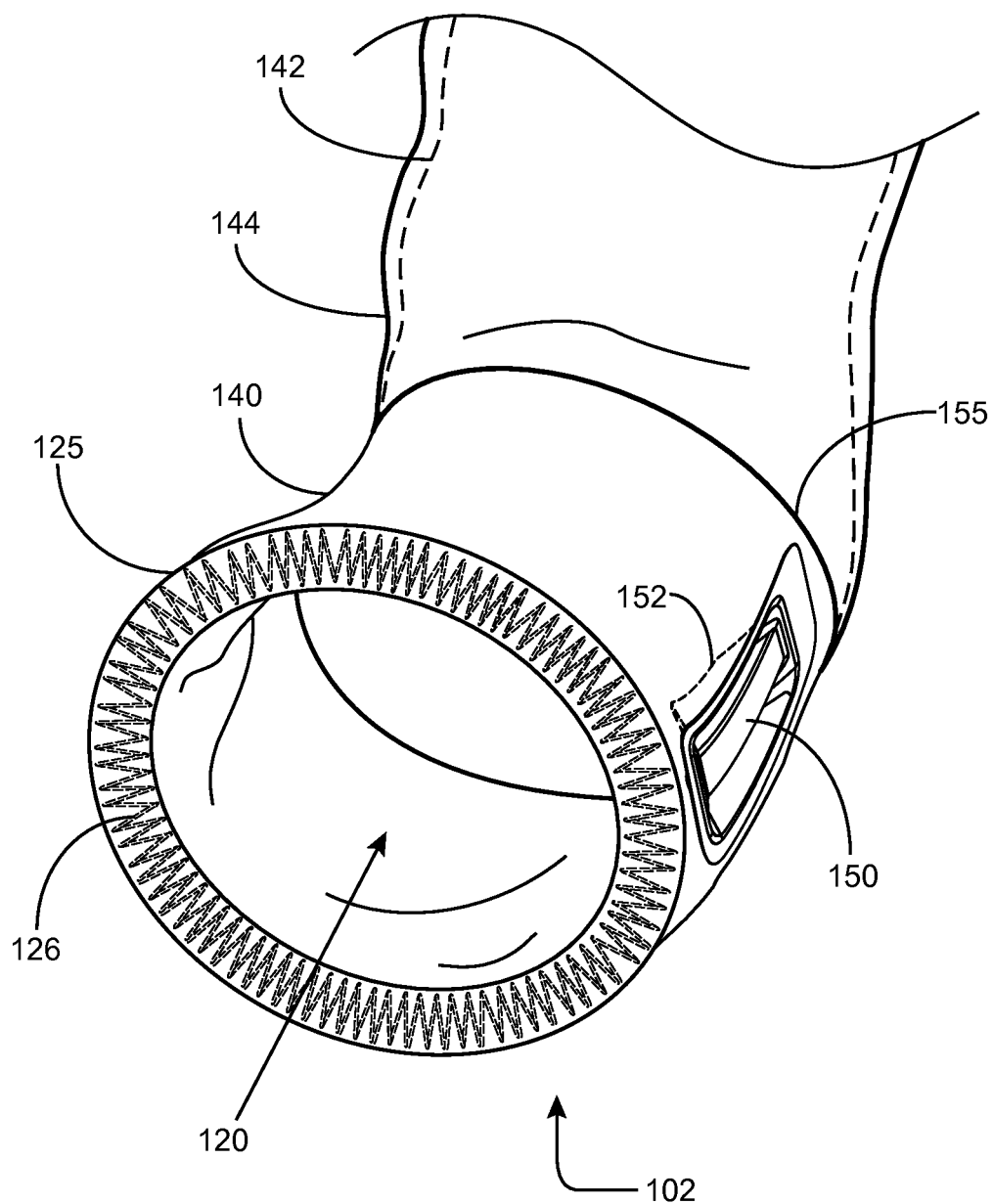
FIG. 9 illustrates a close-up perspective view of a device that includes a molded window measurement feature.

FIG. 9 illustrates a close-up perspective view of a subject device in accordance with some embodiments of the invention. The proximal end 102 is shown for reference. The depicted device includes a surgical pouch 140 that comprises an inner pouch 142 as well as an outer pouch 144. As shown, the inner pouch 142 and the outer pouch 144 originate at an origination point 155 that is located at a position along the body of the surgical pouch 140. The depicted device includes a measurement feature 150 in the form of a molded window placed along the body of the surgical pouch 140. The inwardly-directed components 152 of the molded window 150 protrude into the interior portion of the surgical pouch 140, and a portion of the patient's exposed gastrointestinal body part may be placed between the inwardly-directed components 152 to facilitate measurements of, e.g., oxygen saturation during use of the device. In the depicted embodiment, a measuring component 154 of a monitoring device (not shown) is engaged with the inwardly-directed components 152 of the molded window 150.

Figure 10:
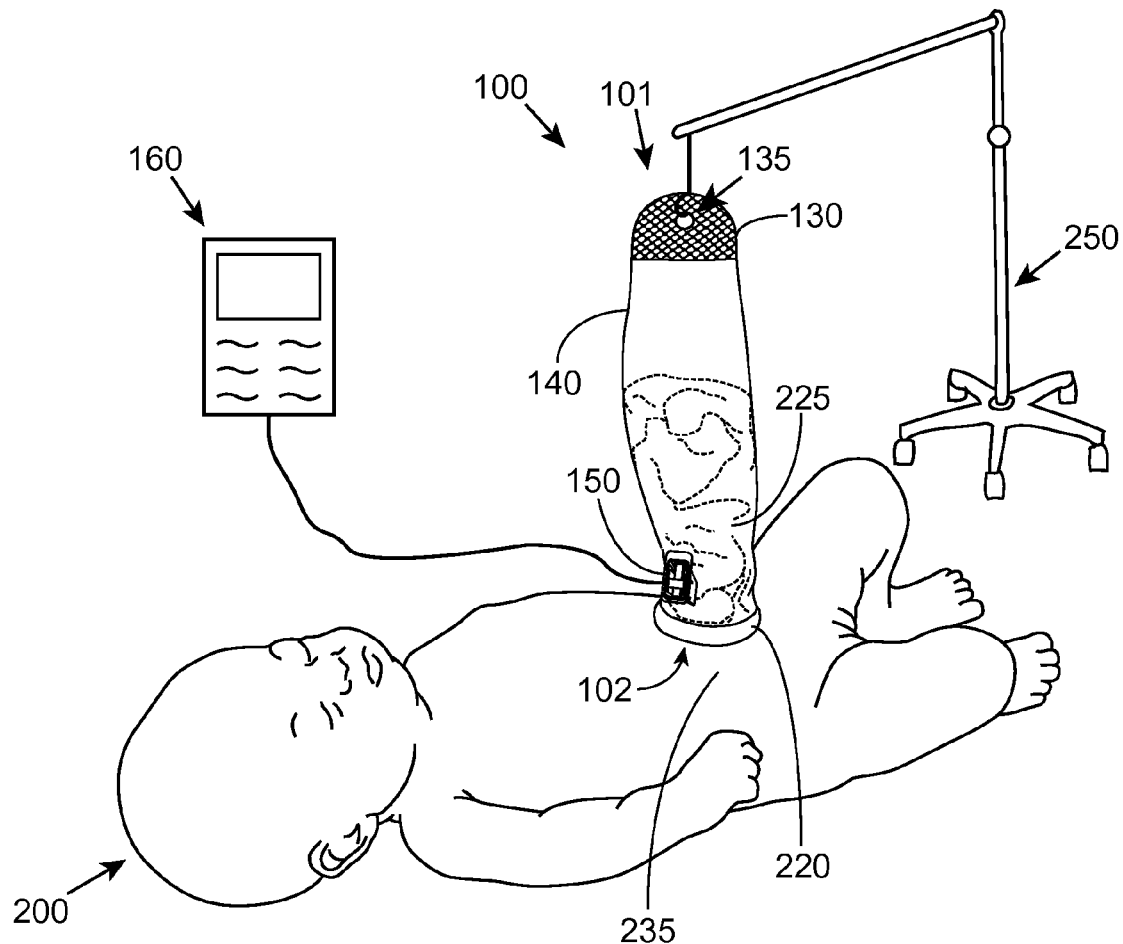
FIG. 10 illustrates a perspective view of the device shown in FIG. 1 containing exposed internal body parts. Also depicted is a monitoring device used to monitor the oxygen saturation of the exposed internal body parts during the insertion process via a molded window measurement feature.

FIG. 10 illustrates a perspective view of a subject device during use, according to some embodiments of the invention. Distal end 101 and proximal end 102 are shown for reference purposes. As shown, device 100 includes a surgical pouch 140. Surgical pouch 140 includes a coupling component 130 with a hole 135 that can be coupled to an external support structure 250 to support the device in a desirable position.

An exposed gastrointestinal body part 225 of a patient 200 has been inserted into the surgical pouch 140 and contained therein. An opening (not shown) of the device is located at the proximal end 102 and inserted within a surgical opening 220 in the abdomen 235 of the patient 200. The surgical pouch 140 also includes a measurement feature 150 in the form of a molded window into which an exposed gastrointestinal body part 225 of the patient 200 may be placed. As depicted in FIG. 10, a monitoring device 160, such as, e.g., a pulse oximeter, may be used to monitor the exposed gastrointestinal body part 225 during the insertion process via the measurement feature. In the depicted embodiment, a measurement component of the monitoring device 160 is attached to the molded window 150 to facilitate a measurement of the oxygen saturation of the exposed gastrointestinal body part 225 that has been placed between the inwardly-directed components of the molded window.

Figure 11:
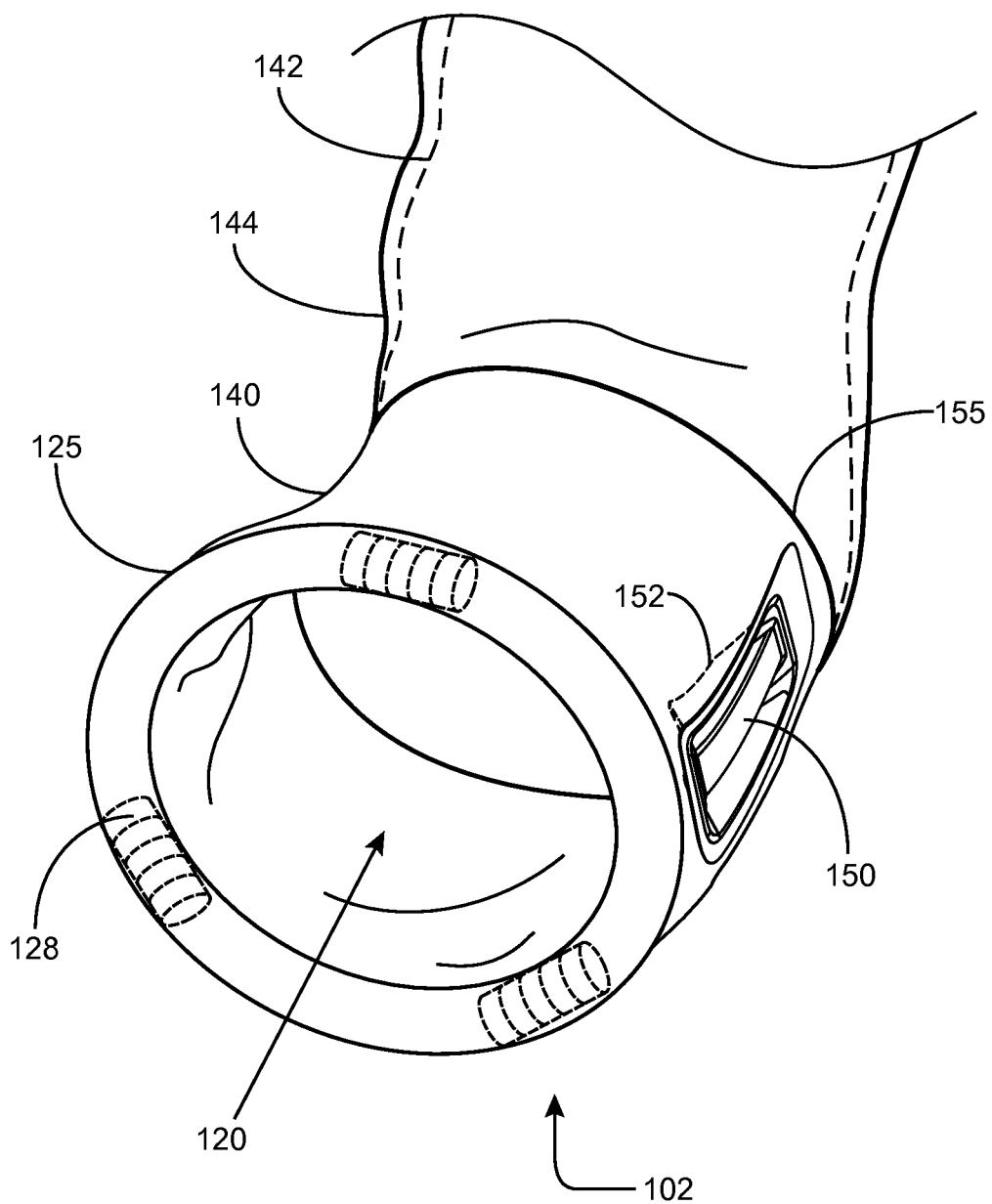
FIG. 11 illustrates a close-up perspective view of a device that includes a molded window measurement feature and a securing component that includes three magnetic components disposed inside the ring of the securing component.

FIG. 11 illustrates a close-up perspective view of a subject device in accordance with some embodiments of the invention. The proximal end 102 is shown for reference. The depicted example of a device of the present disclosure includes a surgical pouch 140 that comprises an inner pouch 142 as well as an outer pouch 144. As shown, the inner pouch 142 and the outer pouch 144 originate at an origination point 155 that is located at a position along the body of the surgical pouch 140. The depicted device includes a measurement feature 150 in the form of a molded window placed along the body of the surgical pouch 140. The inwardly-directed components 152 of the molded window 150 protrude into the interior portion of the surgical pouch 140, and a portion of the patient's exposed gastrointestinal body part may be placed between the inwardly-directed components 152 to facilitate measurements of, e.g., oxygen saturation during use of the device. In the depicted embodiment, a measuring component 154 of a monitoring device (not shown) is engaged with the inwardly-directed components 152 of the molded window 150. The depicted device also includes a securing component 125 that includes three magnetic components 128, which are in this example provided as clusters of magnetic discs. In this example, magnetic components 128 are provided within a lumen of the securing component 125 and are substantially evenly spaced along the circumference of the securing component 125. In such embodiments, the device can optionally be used in combination with a second ring comprising magnetic components (not shown) as described in the examples below.

Figure 12:
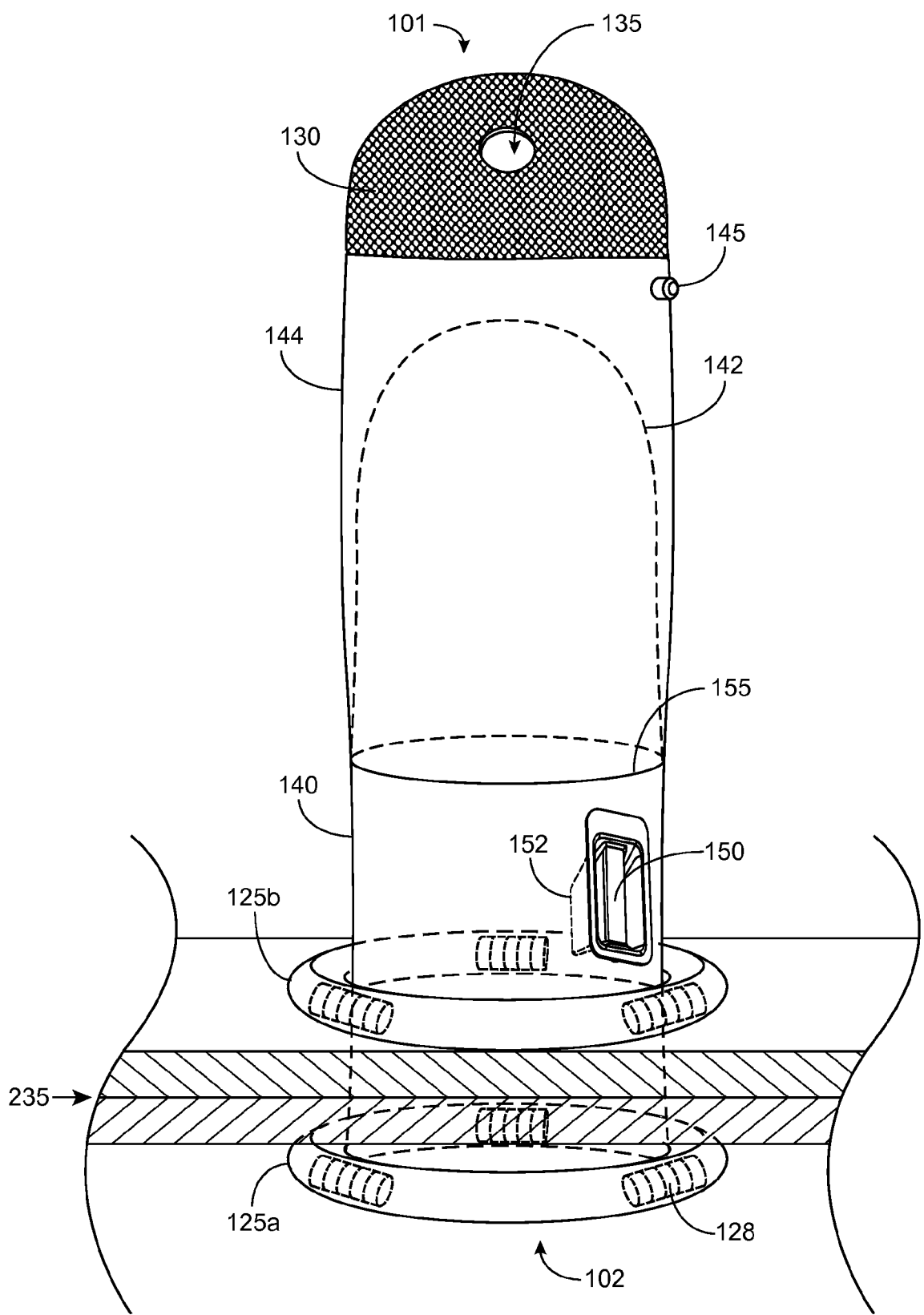
FIG. 12 illustrates a perspective view of a device that has a securing component that comprises a first ring and a second ring that each include three magnetic components. As shown, the first ring is positioned inside a patient's body, and the second ring is placed around the outside of the device and against the patient's skin on the outside of the patient's body.

FIG. 12 illustrates a perspective view of a subject device during use, according to some embodiments of the invention. Distal end 101 and proximal end 102 are shown for reference purposes. The depicted device includes a surgical pouch 140 that includes an inner pouch 142 and an outer pouch 144. Outer pouch 144 includes a coupling component 130 with a hole 135 that can be coupled to an external support structure (not shown) to support the device in a desirable position. The depicted device also includes a securing component that comprises a first ring 125a which is adapted for use with a second ring 125b, where the first ring 125a and second ring 125b are adapted for positioning on opposite sides of the patient's abdominal wall 235. In this example, each of the first ring 125a and the second ring 125b include three clusters of magnetic components 128. In use, the second ring may be periodically lifted or pulled in a direction away from the patient's body to stretch the abdominal wall 235 and the abdominal cavity by exerting a magnetic attraction force on the first ring 125a, and thereby pulling on the first ring 125a when the second ring 125b is lifted or pulled. Such pulling and stretching may aid in the reduction of the one or more gastrointestinal body parts that have been placed within the surgical pouch.

Methods

Methods in accordance with embodiments of the invention may generally be used to contain an exposed gastrointestinal body part of a patient and to facilitate its insertion into the patient's body using a subject device, and to simultaneously monitor the oxygen saturation of the exposed gastrointestinal body part via a measurement feature on the device. For example, in some embodiments, the subject methods involve placing an exposed gastrointestinal body part of the patient inside the surgical pouch of a subject device and securing the securing component of the device inside a surgical opening on the patient. The subject methods further involve placing a portion of the exposed gastrointestinal body part inside a measurement feature that is present on the body of the surgical pouch of the device. The measurement feature, as described above, is adapted to facilitate the attachment of an external monitoring device, such as a pulse oximeter. As such, aspects of the methods involve placing a measuring component of a monitoring device on the measurement feature and taking a measurement of the gastrointestinal body part that has been place therein. In certain embodiments, the methods involve placing a pulse oximeter on the measurement feature and measuring the oxygen saturation of the gastrointestinal body part that has been placed therein. In this way, proper blood flow and oxygenation of the gastrointestinal body part can be monitored during use of the device.

In some embodiments, the subject methods involve inserting the exposed gastrointestinal body part into the patient's body using gravity and/or manual insertion by a caregiver. For example, in some embodiments, the exposed gastrointestinal body part is placed inside the device, and a portion of the exposed gastrointestinal body part is placed within a measurement feature on the device to facilitate measuring the oxygen saturation of the exposed gastrointestinal body part during use of the device. In some embodiments, the device is mounted on an external support structure so that the distal end of the device is above the proximal end of the device, and the force of gravity causes the exposed gastrointestinal body part to move towards the proximal end of the device and into the patient's body. In some embodiments, a caregiver may manually push the exposed gastrointestinal body part towards the proximal end of the device and/or into the surgical opening to place the exposed gastrointestinal body part inside the patient's body. During use of the device, the oxygen saturation of the exposed gastrointestinal body part that has been placed in the device can be monitored by a caregiver via the measurement feature.

In some embodiments, the subject methods involve inserting an exposed gastrointestinal body part into the patient's body using a device having a surgical pouch that includes an inner pouch as well as an outer pouch, as described above, and using positive pressure to facilitate insertion of the exposed gastrointestinal body part into the patient's body. For example, in some embodiments, following placement of the exposed gastrointestinal body part inside the surgical pouch, a pressurized fluid or gas, such as pressurized air, may be introduced into the space between the inner pouch and the outer pouch via a port in the outer pouch to pressurize the outer pouch. Pressurizing the outer pouch exerts a positive pressure force on the inner pouch, and thereby facilitates a reduction in the volume of the inner pouch. As the volume of the inner pouch is reduced, the gastrointestinal body part is gradually moved towards the opening of the device and inserted into the body of the patient. In some embodiments, the methods further involve placing a lubricant (e.g., water or glycerol) in the space between the inner pouch and the outer pouch to facilitate the movement of the inner pouch over the internal surface of the outer pouch.

In some embodiments, the subject methods involve gradually modulating the pressure inside the device. For example, in some embodiments, the subject methods involve gradually increasing the pressure inside the device over time, such that the force exerted on the inner pouch gradually increases with time. In some embodiments, the subject methods involve gradually decreasing the pressure inside the device over time, such that the force exerted on the inner pouch gradually decreases with time, or subsides. In certain embodiments, the subject methods involve periodically increasing, or spiking the pressure inside the device, followed by periods of decreased pressure. As such, the subject methods provide for exerting a larger force on the inner pouch (generated during pressure spikes) to encourage insertion of the gastrointestinal body part into the patient's body, followed by periods of reduced force, which allow the gastrointestinal body part to rest, or recover, thereby avoiding damage to the gastrointestinal body part that could be caused by excessive application of pressure. In some embodiments, a specified pressure is applied to the outer pouch and is maintained for the duration of the procedure, i.e., the pressure inside the device is not modulated over time.

In some embodiments, the subject methods involve placing a portion of the exposed gastrointestinal body part inside a measurement feature that is present on the body of the surgical pouch of the device. The measurement feature, as described above, is adapted to facilitate the attachment of an external monitoring device, such as a pulse oximeter. As such, in some embodiments the subject methods involve placing a measuring component of a monitoring device on the measurement feature and taking a measurement of the gastrointestinal body part that has been placed therein, either before, during or after applying positive pressure to the space between the inner and outer pouches of the device to facilitate insertion of the exposed gastrointestinal body part into the patient. In certain embodiments, the methods involve placing a pulse oximeter on the measurement feature and measuring the oxygen saturation of the gastrointestinal body part that has been placed therein. In this way, proper blood flow and oxygenation of the gastrointestinal body part can be monitored during use of the device, either before, during or after positive pressure is applied to the device.

In certain embodiments, the subject methods further involve coupling the device to a support structure. In such embodiments, following placement of the gastrointestinal body part inside the device, the distal end of the device may be coupled to a support structure via a coupling component. In such embodiments, the device is generally positioned so that it hangs above the patient and the natural force of gravity, along with any applied pressure, helps to move the gastrointestinal body part towards the opening of the device and into the patient's body. In some embodiments, the support structure is adjustable, and the method involves positioning the support structure in a suitable position and/or configuration such that the device is suspended in a suitable position above the patient's body.

Kits

Also provided are kits that at least include the subject systems and devices or components thereof, e.g., as described above, and instructions for how to use the devices to contain an exposed gastrointestinal body part and insert the gastrointestinal body part into the body of the patient. In some instances, the kits may include multiple devices having different sizes and/or dimensions, such that an appropriately-sized device may be selected for a given patient, application or procedure. In some instances, the kits may include one or more support structures to be used for hanging and/or positioning the device above a patient's body. In some embodiments, the subject kits may include a monitoring device, such as a pulse oximeter, that can be used to monitor an exposed gastrointestinal body part that is placed inside the subject device.

In some embodiments, the kits may include components for sterilizing the devices, sterilizing or preparing a portion of the patient's body for a procedure, or both. In certain embodiments, the kits may contain a lubricant that can be introduced between the inner pouch and the outer pouch to facilitate movement of the inner pouch over the internal surface of the outer pouch. Various components of the subject devices may be packaged as desired, e.g., either together or separately.

The instructions for using the systems and devices as discussed above are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer-readable storage medium, e.g., a digital storage medium, e.g., a CD-ROM, diskette, etc. The instructions may take any form, including complete instructions for how to use the systems and devices or as a website address with which instructions posted on the Internet may be accessed.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for containing and monitoring an exposed gastrointestinal body part of a patient, the method comprising:
   placing the exposed gastrointestinal body part inside of a device to contain the exposed gastrointestinal body part, wherein the device comprises:
     an inner pouch for containing the exposed gastrointestinal body part of the patient;
     an outer pouch for exerting positive pressure on the inner pouch to facilitate the insertion of the exposed gastrointestinal body part into the patient's body, wherein the outer pouch comprises a port that provides access to an area between the inner pouch and the outer pouch;
     a measurement feature adapted to facilitate a measurement of the oxygen saturation of the exposed gastrointestinal body part; and
     a securing component adapted to secure an opening of the device to a surgical opening on the patient, the securing component comprising a ring positioned around a perimeter of the opening of the device, wherein the ring comprises a magnetic component;
   placing a portion of the exposed gastrointestinal body part into the measurement feature of the device;
   monitoring the oxygen saturation of the exposed gastrointestinal body part via the measurement feature;

placing a lubricant in the area between the inner pouch and the outer pouch of the device; and pressurizing the outer pouch of the device to facilitate insertion of the exposed gastrointestinal body part into the patient's body.

2. The method according to claim 1, wherein monitoring the oxygen saturation of the exposed gastrointestinal body part via the measurement feature comprises attaching a pulse oximeter to the measurement feature.

3. The method according to claim 1, wherein the ring is collapsible for insertion into the surgical opening on the patient, and wherein the ring is resilient, such that the ring returns to an un-collapsed state after insertion into the surgical opening on the patient.

4. The method according to claim 1, wherein the device further comprises a coupling component disposed at a distal end of the device and adapted to couple the distal end of the device to a support structure, and wherein the method further comprises coupling the coupling component to a support structure.

5. The method according to claim 4, wherein the coupling component of the device further comprises a reinforcing material.

6. The method according to claim 1, wherein the measurement feature comprises a finger-like projection that is adapted to receive an exposed gastrointestinal body part therein.

7. A method for containing and monitoring an exposed gastrointestinal body part of a patient, the method comprising:

placing the exposed gastrointestinal body part inside of a device to contain the exposed gastrointestinal body part, wherein the device comprises:

a surgical pouch for containing a gastrointestinal body part of the patient, wherein the surgical pouch comprises a measurement feature adapted to facilitate a measurement of the oxygen saturation of the exposed gastrointestinal body part, and wherein the measurement feature comprises a material that is different from the material of the surgical pouch; and a securing component adapted to secure an opening of the device to a surgical opening on the patient, the securing component comprising a ring positioned around a perimeter of the opening of the device, wherein the ring comprises a magnetic component;

placing a portion of the exposed gastrointestinal body part into the measurement feature of the device; and monitoring the oxygen saturation of the exposed gastrointestinal body part via the measurement feature, wherein monitoring the oxygen saturation of the exposed gastrointestinal body part via the measurement feature comprises attaching a pulse oximeter to the external surface of the measurement feature.

8. The method according to claim 7, wherein the ring is collapsible for insertion into the surgical opening on the patient, and wherein the ring is resilient, such that the ring returns to an un-collapsed state after insertion into the surgical opening on the patient.

9. The method according to claim 7, wherein the device further comprises a coupling component disposed at a distal end of the device and adapted to couple the distal end of the device to a support structure, and wherein the method further comprises coupling the coupling component to a support structure.

10. The method according to claim 9, wherein the coupling component of the device further comprises a reinforcing material.

11. The method according to claim 7, wherein the measurement feature comprises a finger-like projection that is adapted to receive an exposed gastrointestinal body part therein.

* * * * *